(12) United States Patent
Parton et al.

(10) Patent No.: US 9,464,023 B2
(45) Date of Patent: Oct. 11, 2016

(54) PROCESS FOR THE PREPARATION OF FORMYLVALERIC ACID AND ADIPIC ACID

(71) Applicant: DSM IP ASSETS B.V., Heerlen (NL)

(72) Inventors: Rudy Francois Maria Jozef Parton, Echt (NL); Michele Catherine Christianne Janssen, Echt (NL); Barthel Engendahl, Echt (NL); Johannes Gerardus De Vries, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/760,885

(22) PCT Filed: Jan. 16, 2014

(86) PCT No.: PCT/EP2014/050764
§ 371 (c)(1),
(2) Date: Jul. 14, 2015

(87) PCT Pub. No.: WO2014/111446
PCT Pub. Date: Jul. 24, 2014

(65) Prior Publication Data
US 2016/0221913 A1  Aug. 4, 2016

Related U.S. Application Data

(60) Provisional application No. 61/754,273, filed on Jan. 18, 2013.

(30) Foreign Application Priority Data

Jan. 18, 2013 (EP) .................................. 13151816
Feb. 22, 2013 (EP) .................................. 13156303

(51) Int. Cl.
*C07C 51/12* (2006.01)
*C07D 201/08* (2006.01)
*C07C 51/373* (2006.01)
*C07C 51/42* (2006.01)

(52) U.S. Cl.
CPC .............. *C07C 51/373* (2013.01); *C07C 51/12* (2013.01); *C07C 51/42* (2013.01)

(58) Field of Classification Search
CPC ..... C07C 51/12; C07C 51/42; C07C 51/373; C07D 201/08
USPC ......... 562/517, 522, 577; 560/177; 540/538, 540/539
See application file for complete search history.

(56) References Cited

FOREIGN PATENT DOCUMENTS

| EP | 1251122 A1 | 10/2002 |
|---|---|---|
| WO | 9426688 A1 | 11/1994 |
| WO | 2012134397 A1 | 10/2012 |

OTHER PUBLICATIONS

International Search Report from corresponding PCT/EP2014/050764, mailed Apr. 28, 2014.

*Primary Examiner* — Sikarl Witherspoon
(74) *Attorney, Agent, or Firm* — McBee Moore Woodward & Vanik IP, LLC

(57) ABSTRACT

The invention relates to a process for the production of 5-formylvaleric acid and adipic acid or esters thereof from an isomeric mixture of pentenoic acid or esters thereof said mixture comprising at least 4-pentenoic acid or esters thereof, and further comprising 3-pentenoic acid and/or 2-pentenoic acid or esters thereof.

The process allows for efficient production of two different intermediates for producing polyamide using a single process, with good selectivity, little waste, in an economically efficient fashion. The process is very suitable to use an isomeric pentenoic acid mixture obtained from valerolactone, and can be used to produce renewable polyamide intermediates using a single process.

11 Claims, No Drawings

PROCESS FOR THE PREPARATION OF FORMYLVALERIC ACID AND ADIPIC ACID

CROSS REFERENCE TO RELATED APPLICATIONS

This application is a §371 National Stage Application of PCT/EP2014/050764, filed 16 Jan. 2014, which claims priority to U.S. 61/754,273, filed 18 Jan. 2013, EP 13151816.9, filed 18 Jan. 2013 and EP 13156303.3, filed 22 Feb. 2013.

BACKGROUND

1. Field of the Invention

The present invention relates to a process for the preparation of formyl valeric acid and adipic acid or esters thereof.

2. Description of Related Art

The current production of caprolactam and adipic acid is based on processes requiring a lot of energy and leads to release of greenhouse gases such as CO2 and NOx. Thus, there is a great incentive to replace these processes by other processes leading to less use of energy and in which the amount of greenhouse gases released is substantially less.

A known production route to caprolactam proceeds via 5-formylvaleric acid, which can be made from butadiene. WO94/26688 discloses a process to produce linear aldehydes such as 5-formylvaleric acid from an isomeric mixture of methyl pentenoates. The process of WO94/26688 starts with an isomerisation step in order to increase the amount of methyl-4-pentenoate, and proceeds with a non-isomerising hydroformylation step of the isomerised mixture of methyl pentenoates acids using a Rh catalyst to produce a mixture of 5-formyl valeric acid and remaining methylpentenoates consisting mainly methyl-3-pentenoate and some methyl-2-pentenoate. Next, the 5-formyl valeric acid is separated from the remaining methyl pentenoates and the remaining methyl pentenoates are fed back to the isomerisation step.

EP1251122-A1 relates to a process for the preparation of ε-caprolactam starting from butadiene, carbon monoxide, hydrogen and ammonia, by (1) carbonylating butadiene in the presence of an alkanol and a catalyst comprising palladium, a multidentate phosphine ligand and an acidic co-catalyst to produce alkyl-4-, alkyl-3- and alkyl-2-pentenoate; (1') optionally isomerising the alkyl-3- and/or alkyl-2-pentenoate into alkyl-4-pentenoate; (2) hydroformylating the alkyl-4-, alkyl-3- and alkyl-2-pentenoate in the presence of a catalyst comprising rhodium and an organic phosphorous containing ligand to produce alkyl-5-formylvalerate; (3) reductively aminating alkyl-5-formylvalerate in the presence of a hydrogenation catalyst comprising ruthenium on a carrier to produce ε-caprolactam and ε-caprolactam precursors; and (4) optionally converting ε-caprolactam precursors at elevated temperature into ε-caprolactam.

A problem with the isomerisation of pentenoic acids (or esters) is that the equilibrium constant favours the formation of 3-pentenoic acid, and that relatively little 4 pentenoic acid is formed. Thus, a problem of WO94/26688 is that the recycle step is very inefficient since with every recycle step only a small fraction of the remaining 2 and 3 pentenoate esters is isomerized into 4-pentenoate ester and subsequently converted to methyl 5-formylvaleriate This means that in the process of WO94/26688 a substantial fraction consisting of 2 and 3 pentenoic acid esters is more or less perpetually recirculated. This is of course economically undesirable.

An option would be to simply discard any remaining 2 and 3 pentenoic esters but this would result in an unacceptable waste. An alternative solution suggested by WO94/26688 is to enrich the starting mixture in methyl 4-pentenoate by separating it from the other isomers using distillation. However, it is known in the art [ref] that due to their similarity it is very difficult to separate methyl 4-pentenoate from methyl 2- and 3-pentenoate. Moreover, this would mean extra cost due to in expensive distillation equipment.

It is an aim of the invention to provide a single process to make both formylvaleric acid and adipic acid or esters thereof from an isomeric mixture of pentenoic acids or esters. It is another aim to provide a process which allows for efficient use of an isomeric (alkyl) pentenoic acid mixture in making polyamide intermediates, which process is preferably simple and/or affords good yield and/or selectivity, and/or which results in little or no wasted side products.

SUMMARY

In one aspect the invention provides a process for the production of 5-formylvaleric acid and adipic acid or esters thereof from an isomeric mixture of pentenoic acid or esters thereof said mixture comprising at least 4-pentenoic acid or esters thereof, and further comprising 3-pentenoic acid and/or 2-pentenoic acid or esters thereof, the process comprising:

(a) subjecting said isomeric mixture to a hydroformylation reaction comprising a hydroformylation catalyst which is non-isomerizing towards the pentenoic acid or esters thereof to obtain a mixture comprising 5-formylvaleric acid or esters thereof and further comprising 3-pentenoic acid and/or 2-pentenoic acid, or esters thereof;

(b) separating the 3-pentenoic acid and/or 2-pentenoic acid, or esters thereof from the 5-formylvaleric acid or esters thereof;

(c) subjecting the separated pentenoic acids or esters thereof to a carbonylation reaction comprising an isomerizing carbonylation catalyst to obtain adipic acid or esters thereof;

(d) optionally isolating the adipic acid or ester thereof; and (e) optionally isolating the separated 5-formylvaleric acid or esters thereof.

The isomeric mixture of pentenoic acid or esters thereof comprises 4-pentenoic acid or esters thereof and further comprises 3-pentenoic acid and/or 2-pentenoic acid or esters thereof. Preferably said isomeric mixture comprises 4-pentenoic acid, 3-pentenoic acid, and 2-pentenoic acid or esters thereof.

The amount of 2-pentenoic acid or esters thereof in the isomeric mixture, prior to the hydroformylation reaction, preferably ranges between 5 and 25 mol % relative to the total amount of pentenoic acid or esters thereof, more preferably between 10 and 20 mol %.

The amount of 3-pentenoic acid or esters thereof in the isomeric mixture, prior to the hydroformylation reaction, preferably ranges between 40 and 80 mol % relative to the total amount of pentenoic acid or esters thereof, more preferably between 50 and 75 mol %.

The amount of 4-pentenoic acid or esters thereof in the isomeric mixture, prior to the hydroformylation reaction, preferably ranges between 5 and 95 mol %, more preferably between 20% and 80 mol %, between 30 and 70 mol %, even more preferably between 40 and 60 mol %.

DETAILED DESCRIPTION OF A PREFERRED EMBODIMENT

In a preferred embodiment the isomeric mixture of pentenoic acid or esters is obtained from gamma valerolactone by subjecting said valerolactone to an acid- or base-catalysed ring opening reaction. An advantage of using valerolactone as source of the isomeric mixture is that two different intermediates for making polyamide can be produced from the same compound. Another advantage of using gamma valerolactone is that the resulting isomeric mixture is rich in 4-pentenoic acid or esters thereof as compared to starting from butadiene which will almost exclusively result in 3-pentenoate. This may avoid the cumbersome isomerization reaction to convert the 3-pentenoate into the isomeric mixture. The ring opening reaction may be carried out in a suitable solvent, such as alcohols. More preferably the ring-opening is carried out without solvent. Alternatively, the ring opening reaction may be carried out in the gas phase process, preferably in the presence of an alcohol. If the ring opening is carried out in the presence of an alcohol, pentenoic acid alkyl esters may be produced. For example, if the alcohol is methanol, methyl pentenoates are formed. Ring opening reactions of lactons are described in U.S. Pat. No. 5,144,061 and U.S. Pat. No. 4,740,613. Suitable catalysts for the ring opening reaction include acidic oxides of group III or IV and subgroups IV and VI of the periodic table, such as silica in the form of silica gel, kieselguhr or quartz, as well as titanium dioxide, phosphorus pentoxide, alumina, and molybdenum oxides. The amount of 4-pentenoic acid or esters obtained by ring opening of gamma valerolactone may depend on the type of catalyst. For example, if the ring opening reaction is base-catalysed, the amount of 4-pentenoic acid is usually higher than when the reaction is acid-catalysed.

An advantage of using gamma valerolactone (5-methyl-butyrolactone) as the source of the isomeric mixture is that it may be obtained from levulinic acid, which in turn may be obtained from biomass. This advantageously allows for the production of two different intermediates for making polyamides that are both renewable in one process.

Therefore, in an embodiment the valerolactone is obtained from levulinic acid in a hydrogenation reaction. Hydrogenation of levulinic acid to gamma valerolactone is described for example in WO2012175439. Suitable catalysts include Ru, or Pt on supports.

In a further embodiment the 5-formylvaleric acid or ester thereof is used to produce caprolactam by converting said formylvaleric acid or ester thereof into caprolactam in a reductive amination reaction, followed by ring-closing. The reductive amination may be conveniently carried out using a heterogeneous metal catalyst such as Ru/C or Ru/TiO$_2$ or Ra—Ni or Ra—Co or Pd/C. The ring-closure is performed by heating the 6-aminohexanoic acid or ester.

The 5-formylvaleric acid can also be used to make adipic acid in an oxidation reaction. This reaction may be catalysed by an enzyme, such as an aldehyde dehydrogenase. The reaction can also be catalyzed by a metal catalyst using oxygen as the oxidant.

The hydroformylation reaction is carried out using a catalyst which causes no or negligible isomerization of the double bonds of the isomeric pentenoic acids or esters thereof. A preferred catalyst system comprises rhodium. Any hydroformylation catalyst that is devoid of isomerizing activity and which gives rise to high yields of aldehyde with a high normal/branched ratio can in principle be used. In practice it will be best to use a rhodium catalyst which comprises monodentate phosphine ligands or bidentate phosphine ligands. Both arylphosphines as well as alkyl-phosphines can be used. Preferred catalyst systems comprise a monodentate or bidentate phosphine ligand. Preferably the monodentate ligand is water-soluble, An example of such a ligand is tris-sodium tris-(m-sulfonato-phenyl)phosphine. Good results may also be obtained with tris-sodium (tris-carboxylato-phenyl)phosphine. Surprisingly good results may be obtained using a catalyst made from Rh(CO)$_2$(acac) and a large excess of water-soluble triarylphosphines. Ligand/rhodium ratios may vary between 20-250; more preferably between 50-200. The hydroformylation reaction is preferably carried out in an organic-aqueous two phase reaction medium. The organic phase may be formed by the starting pentenoic acids or esters and/or the product of the hydroformylation reaction. Said organic phase may also contain a water-immiscible solvent, such as toluene. In an organic-aqueous two phase hydroformylation reaction, the 4-pentenoic acid or ester thereof may be converted essentially exclusively, whilst the 3-pentenoic acids or esters thereof remain unconverted, and the 2-pentenoic acids or esters thereof may be partially unconverted and partially converted into valeric acid or ester.

The process of the invention comprises separating the 3-pentenoic acid and/or 2-pentenoic acid or esters thereof—that is, any remaining pentenoic acids—from the 5-formylvaleric acid or esters thereof. This results in two fractions, a first fraction enriched in 2 and/or 3 pentenoic acid or esters thereof and a second fraction enriched in 5-formylvaleric acid or esters thereof. The first fraction is used to produce adipic acid or esters thereof. The second fraction contains the valuable 5-formylvaleric acid or esters thereof. In the context of the invention "separating the 3-pentenoic acid and/or 2-pentenoic acid or esters thereof from the 5-formylvaleric acid or esters thereof" does not necessarily mean that these compounds must be completely separated. The first fraction comprising 2 and/or 3-pentenoic acid esters thereof may comprise some formyl valeric acid, preferably less than 10 wt %, more preferably less than 5 wt % relative to the total dry weight of the fraction. Similarly, the second fraction may comprise some pentenoic acids or esters thereof, preferably less than 10 wt %, more preferably less than 5 wt %, also relative to the total dry weight of the fraction. If the hydroformylation reaction comprises an organic-aqueous two phase reaction medium, said two phases (which are present in the resulting reaction mixture) are separated. The aqueous phase, comprising the catalyst, may be recycled back to the hydroformylation reaction. The organic phase, comprising remaining pentenoic acids or esters thereof and comprising 5-formylvaleric acid, may be subjected to distillation. If the reaction comprises a solvent, such solvent is preferably removed by distillation, followed by the mixture of 3-pentenoic acids or esters, 2-pentenoic acid or esters, and 5-formylvaleric acid, ester, with optionally a small amount of unconverted 4-pentenoic acid or ester. Finally, the pure 5-fromyl-valeric acid or ester can be distilled.

After the hydroformylation reaction, the resulting mixture comprising remaining 2- and/or 3-pentenoic acids or esters thereof, and optionally small amounts of 5-formylvaleric acid or esters thereof, which mixture may further comprise traces of 4-pentenoic acid or esters thereof, is subjected to an isomerising hydroxycarbonylation or alkoxycarbonylation reaction. In this reaction, preferably all remaining pentenoic acids or esters thereof are converted to adipic acid or, mono-alkyl adipate, and/or dialkyl adipate, depending on if the acids or the esters were used and if the carbonylation reaction is performed in the presence of water, or an alcohol. The product may contain some valeric acid or ester, which is easily removed by distillation.

Carbonylation reactions of isomeric mixture of pentenoic acids are for example described in WO2012/134397. Carbonylation reactions of mixtures of 2-methylpentenoate and 3-methylpentenoate are described for example in WO2012/131028.

The carbonylation reaction may comprise a source of palladium; a bidentate phosphine ligand of formula I;

R1R2P-R3-R-R4-PR5R6   (I)

wherein P represents a phosphorus atom; R1, R2, R5 and R6 can independently represent the same or different optionally substituted organic groups containing a tertiary carbon atom through which the group is linked to the phosphorus atom; R3 and R4 independently represent optionally substituted lower alkylene groups and R represents an optionally substituted aromatic group; a source of anions derived from an acid with a pKa<3; carbon monoxide; and an OH comprising compound.

The adipic acid or esters thereof obtained in the carbonylation reaction may optionally be isolated by methods known in the art, e.g. by crystallization, solvent extraction, distillation, filtration, or combinations thereof. Likewise, the 5-formylvaleric acid obtained in the hydroformylation reaction may also be isolated by methods known in the art.

EXAMPLES

Example 1

In this example a bi-phasic water-organic system with Rh/TPPTS as the catalyst was compared with Rh/PPh$_3$ in the organic phase under various conditions. The isomeric methylpentenoate mixture was prepared by a ring-opening reaction of γ-valerolactone with methanol in the presence of a heterogeneous acid catalyst in the gas-phase and had the following composition: methyl-2-pentenoate (M2P) 17%, methyl-3-pentenoate (M3P) 65% and methyl-4-pentenoate (M4P) 18%. The conversion of valerolactone to a mixture of methyl pentenoates in step (a) can be done for example in the liquid phase or in the gas phase to deliver a mixture of methyl 2-pentenoate, methyl 3-pentenoate and methyl 4-pentenoate. Such processes are described in WO2005058793, WO2004007421, and U.S. Pat. No. 4,740,613.

Hydroformylation of MP Mixture—Bi-Phasic System

Rh(acac)(CO)$_2$ (1 mg, 3.875 μmol) and TPPTS (330 mg, 0.58 mmol, 150 eq or 44 mg, 0.0775 mmol, 20 eq) were dissolved in 2 mL of water. A solution of 0.5 mL of an isomeric methylpentenoate mixture in 2 mL of toluene was added. The reaction mixture were transferred into glass inserts and were placed in a Biotage Endeavor parallel setup. The reactor was purged 5 times with N$_2$ and successively pressurized to either P$_{CO/H2}$=10 bar or P$_{CO/H2}$=20 bar and heated to T=110° C. or 80° C. The reaction was allowed to proceed overnight. Results are depicted in Table 1, entry 1 and 3.

Hydroformylation of MP Mixture

Rh(acac)(CO)$_2$ (1 mg, 3.875 μmol) and PPh$_3$ (152 mg, 0.58 mmol, 150 eq or 20 mg, 0.0775 mmol, 20 eq) were dissolved in 4 mL of toluene. A mixture of methylpentenoates (0.5 mL) was added, and glass inserts were placed in the Biotage Endeavor parallel setup to be subjected to hydroformylation. The reactor was purged 5 times with N$_2$ and successively pressurized to either P$_{CO/H2}$=10 bar or P$_{CO/H2}$=20 bar and heated to T=110° C. or 80° C. The reaction was allowed to proceed overnight. Results are summarized in Table 1, entry 2 and 4.

The aqueous phases of the hydroformylation reaction mixture obtained in entry 1 was separated from the organic phase and the organic phase was subjected to a methoxycarbonylation reaction, in which remaining methylpentenoates were converted to dimethyl adipate: Pd(OAc)$_2$ (1 mg, 4.4 μmol) and 1,2-Bis(di-tert-butylphosphinomethyl)benzene (8.9 mg, 22 μmol) were dissolved in 3.5 mL of methanol. Methanesulfonic acid (44 μmol) was added to the catalyst solution. Then, the organic phase of the hydroformylation reaction of entry 1 was added and glass inserts were placed in a Biotage Endeavor parallel setup. The reactor was purged 5 times with N$_2$ and successively pressurized to P$_{CO}$=20 bar and heated to T=100° C. The reaction was allowed to proceed for 4 h, and resulted in full conversion of M2P and M3P in dimethyl adipate with a selectivity of 98%.

Example 2

In this example an integrated approach to CAP and DMA was demonstrated, i.e. including distillative separation. This example also shows that no additional solvent (toluene) is needed, which is advantageous from a process intensification point of view.

Rh(acac)(CO)$_2$ (0.5 mg, 1.94 μmol) and TPPTS (165 mg, 0.29 mmol, 150 eq) were dissolved in 2 mL of water. A mixture of methylpentenoates (0.5 mL) was added, and the glass inserts were placed in an Biotage Endeavor parallel setup to be subjected to a hydroformylation reaction. The reactor was purged 5 times with N$_2$ and successively pressurized to either P$_{CO/H2}$=10 bar and heated to T=110° C. The reaction was allowed to proceed overnight. The aqueous and organic phases were separated, and the organic phase comprising the unreacted methylpentenoates M2P and M3P and M5FV was fractionally distilled. The distillate was then subjected to methoxycarbonylation reaction according to Table 2: Pd(OAc)$_2$ (1 mg, 4.4 μmol) and 1,2-Bis(di-tert-butylphosphinomethyl)benzene (8.9 mg, 22 μmol) were dissolved in 3.5 mL methanol. Methanesulfonic acid (44 μmol) was added to the catalyst solution. Then, methylpentenoates were added (obtained as the distillates above) and glass inserts were placed in a Biotage Endeavor parallel setup. The reactor was purged 5 times with N$_2$ and successively pressurized to P$_{CO}$=20 bar and heated to T=100° C. The reaction was allowed to proceed for 4 h. DMA yield was 94%; selectivity to DMA (dimethyladipate) was 98%. By performing the 2 reactions consecutively, the methylpentenoate mixture was converted to 16% M5FV and 78% DMA, next to small amount of branched isomers of formylvaleric acid and DMA.

TABLE 1

| | | | | | | | | | |
|---|---|---|---|---|---|---|---|---|---|
| Rh-catalyzed hydroformylation of an MP mixture (average of duplicates) | | | | | | | | | |
| Entry | Catalyst | Solvent (mL) | T °(C.) | P$_{CO/H2}$ (bar) | M2P (% area) | M3P (% area) | M4P (% area) | M5FV (% area) | Selectivity to n-aldehydes (%) |
| 1 | Rh/TPPTS (1:150) | H$_2$O/Toluene (2/2) | 110 | 10 | 12.5 | 70 | 2.1 | 14.6 | 92 |

TABLE 1-continued

Rh-catalyzed hydroformylation of an MP mixture (average of duplicates)

| Entry | Catalyst | Solvent (mL) | T °(C.) | $P_{CO/H2}$ (bar) | M2P (% area) | M3P (% area) | M4P (% area) | M5FV (% area) | Selectivity to n-aldehydes (%) |
|---|---|---|---|---|---|---|---|---|---|
| 2 | Rh/TPPTS (1:150) | Toluene (4) | 110 | 10 | 0 | 7 | 0 | 18.3 | 19.7 |
| 3 | Rh/TPPTS (1:20) | H$_2$O/Toluene (2/2) | 80 | 20 | 0 | 76 | 0 | 17.4 | 72 |
| 4 | Rh/PPh3 (1:20) | Toluene (4) | 80 | 20 | 0 | 19 | 0 | 14.7 | 18 |

M5FV, 5-formylvaleric acid

TABLE 2

Methoxycarbonylation reaction conditions

| | M2P (% area) | M3P (% area) | M4P (% area) | M5FV (% area) |
|---|---|---|---|---|
| Before distillation | 9.9 | 61 | 2.6 | 9.1 |
| Distillate | 11.8 | 77.7 | 3.6 | 0.48 |
| Distillation residue | 6.3 | 21.7 | 0.3 | 63.2 |

The invention claimed is:

1. Process for the production of 5-formylvaleric acid and adipic acid or esters thereof from an isomeric mixture of pentenoic acid or esters thereof said mixture comprising at least 4-pentenoic acid or esters thereof, and further comprising 3-pentenoic acid and/or 2-pentenoic acid or esters thereof, the process comprising:
   (a) subjecting the isomeric mixture of pentenoic acid to a hydroformylation reaction comprising a hydroformylation catalyst which is non-isomerizing towards the pentenoic acid or esters thereof to obtain a mixture comprising 5-formylvaleric acid or esters thereof and further comprising 3-pentenoic acid and/or 2-pentenoic acid, or esters thereof;
   (b) separating the 3-pentenoic acid and/or 2-pentenoic acid, or esters thereof from the 5-formylvaleric acid or esters thereof;
   (c) subjecting the separated pentenoic acids or esters thereof to a carbonylation reaction comprising a isomerizing carbonylation catalyst to obtain adipic acid or esters thereof;
   (d) optionally isolating the adipic acid or ester thereof; and
   (e) optionally isolating the separated 5-formylvaleric acid or esters thereof.

2. Process according to claim 1 wherein the amount of 4-pentenoic acid or esters thereof in the isomeric mixture is between 5 and 95 mol % relative to the total amount of pentenoic acid or esters thereof.

3. Process according to claim 1 wherein the isomeric mixture of pentenoic acid or esters is obtained from valerolactone by subjecting said valerolactone to an acid- or base-catalysed ring opening reaction.

4. Process according to claim 3 wherein the valerolactone is obtained from levulinic acid in a hydrogenation reaction.

5. Process according to claim 1 wherein the 5-formylvaleric acid or ester thereof is used to produce caprolactam by converting said 5-formylvaleric acid or ester thereof into caprolactam in a reductive amination reaction, followed by ring-closing.

6. Process according to claim 1 wherein hydroformylation catalyst system comprises rhodium.

7. Process according to claim 1 wherein the hydroformylation catalyst system comprises a monodentate or bidentate phosphine ligand.

8. Process according to claim 7 wherein the monodentate ligand comprises tris-sulfonated triphenylphosphine.

9. Process according to claim 1 wherein the hydroformylation reaction is carried out in an organic-aqueous two phase reaction medium.

10. Process according to claim 9 wherein the aqueous phase is separated and recycled back to the hydroformylation reaction.

11. Process according to claim 1 wherein the carbonylation reaction comprises a source of palladium; a bidentate phosphine ligand of formula I;

R1R2P-R3-R-R4-PR5R6      (I)

wherein P represents a phosphorus atom; R1, R2, R5 and R6 can independently represent the same or different optionally substituted organic groups containing a tertiary carbon atom through which the group is linked to the phosphorus atom; R3 and R4 independently represent optionally substituted lower alkylene groups and R represents an optionally substituted aromatic group; a source of anions derived from an acid with a pKa<3; carbon monoxide; and an OH comprising compound.

* * * * *